United States Patent [19]

Baier et al.

[11] 4,092,119
[45] May 30, 1978

[54] ENVIRONMENTAL QUALITY INDICATOR

[75] Inventors: Robert E. Baier, Buffalo; Vito A. DePalma, Tonawanda, both of N.Y.

[73] Assignee: Calspan Corporation, Buffalo, N.Y.

[21] Appl. No.: 595,265

[22] Filed: July 11, 1975

Related U.S. Application Data

[63] Continuation-in-part of Ser. No. 418,500, Nov. 23, 1973, abandoned.

[51] Int. Cl.² .......................................... G01N 31/00
[52] U.S. Cl. ............................. 23/253 TP; 73/27 R; 116/114 AM; 428/173
[58] Field of Search ........... 23/253 TP, 232 E, 254 R, 23/254 E; 116/114 AM; 73/27 R; 338/34; 340/237 R; 264/126; 428/913, 173

[56] References Cited

U.S. PATENT DOCUMENTS

| | | | |
|---|---|---|---|
| 2,567,445 | 9/1951 | Parker | 23/253 TP X |
| 2,741,912 | 4/1956 | Schultze | 116/114 AM |
| 2,908,595 | 10/1959 | Kohl | 428/913 X |
| 2,976,188 | 3/1961 | Kohl | 428/913 X |
| 3,102,300 | 9/1963 | Ruttig | 264/126 |
| 3,198,688 | 8/1965 | Yoder | 428/913 X |
| 3,507,622 | 4/1970 | Tammelin et al. | 23/254 R |
| 3,528,780 | 9/1970 | Radowski | 23/253 TP |
| 3,555,136 | 1/1971 | Rouault | 264/126 X |
| 3,585,004 | 6/1971 | Mast | 23/253 TP |
| 3,681,027 | 8/1972 | Smith | 23/253 TP X |
| 3,698,871 | 10/1972 | Brennan | 116/114 AM X |
| 3,714,562 | 1/1973 | McNerney | 73/27 X |
| 3,744,296 | 7/1973 | Beltzer | 23/253 TP X |
| 3,754,867 | 8/1973 | Guenthor | 23/254 R |
| 3,784,358 | 1/1974 | Drake, Jr. | 23/253 TP |
| 3,924,219 | 12/1975 | Braun | 23/254 EX |

Primary Examiner—Norman Yudkoff
Attorney, Agent, or Firm—Allen J. Jaffe

[57] ABSTRACT

A scuff-resistant, waterproof environmental quality indicator suitable for field use to blot-test unknown spills or wet containers, as field markers of spray distribution, as floating markers of water contamination, as personnel protection badges and as integrating dosimeters. The environmental quality indicator has a topographically varying surface having substantially uniformly located raised portions defining the scuffing and abrasion level and relieved portions beneath the scuffing and abrasion level to protect the indicator formulation from physical environmental hazards, which can produce an initial false indication, while remaining freely exposed to chemical environmental hazards.

20 Claims, 12 Drawing Figures

ENVIRONMENTAL QUALITY INDICATOR

This is a continuation-in-part of application Ser. No. 418,500 filed Nov. 23, 1973, now abandoned.

The invention herein described was made in the course of or under contract with the U.S. Army.

BACKGROUND

The introduction of hazardous chemicals into the environment due to industrial and agricultural activities, or otherwise, has necessitated the development of monitoring systems to protect the environment and the people exposed to the hazardous chemicals. Color indicating paints which give a color change when acted upon by specific chemical agents and resistive paints which undergo a resistive change when acted upon by specific chemical agents have been developed. The use of these paints has been limited by the fact that they are very easily developed by abrasion, gasoline and environmental elements such as rain impaction which give the same initial color and/or resistance change as the hazardous chemicals being monitored or tested for.

In order to protect workers that are exposed to conditions which may be injurious to their health, monitoring devices have been developed to indicate the level of exposure by the workers to certain deleterious conditions. In the case of noise and radiation, badges have been developed to indicate exposure levels. Others workers, such as farm workers, are subject to exposure to hazardous chemicals, such as pesticides, in harmful and even fatal doses. If a worker exposed to pesticides is able to wash off the pesticide within a reasonable time, such as 20 minutes, the effects of exposure to the pesticide can be minimized.

Noise and radiation badges are sensitive to energy waves which give an indication of exposure and thus the indicating element may be protected or shielded from other environmental and occupational hazards. In the case of hazardous chemical detectors, however, the detector must be exposed to environmental and/or occupational hazards in order to be freely exposed to hazardous chemicals in the environment. To be suitable for use as a chemical indicating badge or in other field use applications, the chemical indicating device must function independently of the conditions of the environment of use such as rain and perspiration and must also be durable so that scuffing as by contact with brush, barbed wire, etc. does not give a false indication.

It is an object of this invention to provide a chemical indicator for indicating exposure to pesticides and other hazardous chemicals under field conditions.

It is a further object of this invention to provide an environmental quality indicator which will inherently preserve the detected chemicals to permit archiving or subsequent chemical analysis.

It is an additional object of this invention to provide an environmental quality indicator which will give a qualitative indication of the presence of hazardous chemicals. These objects, and others as will become apparent hereinafter, are accomplished by the present invention.

In applying pesticides, as by spraying from an airplane, it is desirable to spray an entire field, orchard, etc. without having the pesticide sprayed onto adjacent fields, orchards or bodies of water. It is, therefore, desirable to test both the areas intended to be sprayed as well as adjacent areas to determine the presence or absence of pesticides. To obtain this information, indicators may be placed in the field or orchard to be sprayed, at the boundaries of the area to be sprayed and in the surrounding areas as well as on the surface of adjacent bodies of water. If workers are to enter the field or orchard either to check the indicators after spraying or to otherwise work in the field or orchard, it is desirable that the exposure of the workers to the pesticides be indicated. However, since the worker's exposure will be in the environment of a work situation, it is necessary that false readings not be generated, as by scuffing, and, since exposure may cause injury, it is desirable that worker exposure be determined. Because worker exposure as well as the spraying of neighboring fields, orchards and bodies of water may result in lawsuits, it is desirable that a record of exposure be retained.

Other hazardous chemical exposures may take place at night or may be encountered in a monitoring program such as the gaseous and liquid effluents from a factory. In such a situation an active system capable of generating a signal as well as retaining an archivable sample is desired.

All of these objectives, and others, are achieved in the present invention wherein an inert, topographically varying substrate serves as a carrier of reagents, dyes or metallic-loaded paints.

BRIEF DESCRIPTION OF THE DRAWINGS

For a fuller understanding of the present invention, reference should now be had to the following detailed description thereof taken in conjunction with the accompanying drawings wherein.

DESCRIPTION OF THE PREFERRED EMBODIMENTS

Figure 1:
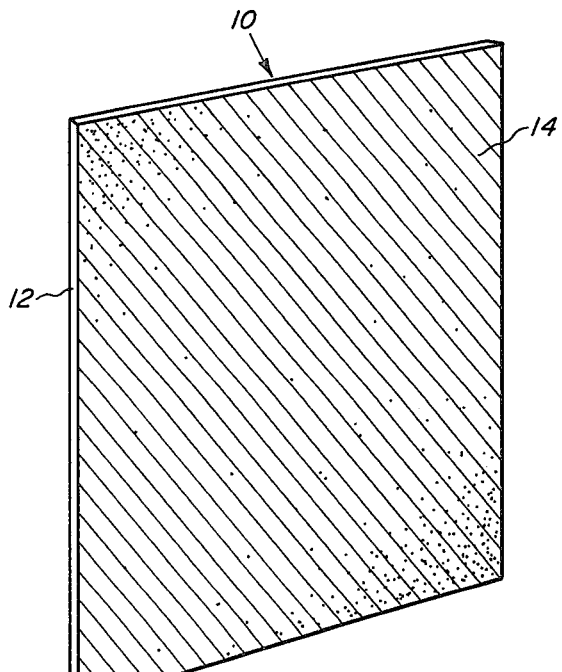
FIG. 1 is an isometric view of an environmental quality indicator.
Figure 2:
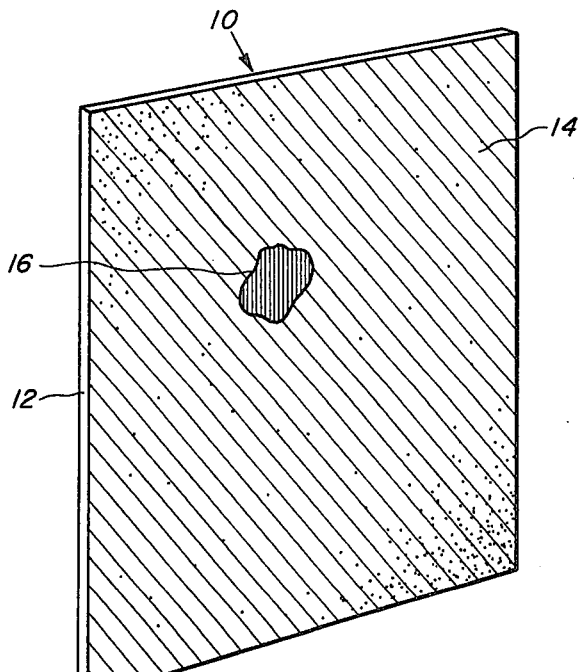
FIG. 2 is a view of the environmental quality indicator of FIG. 1 a few seconds after exposure to a hazardous chemical.
Figure 3:
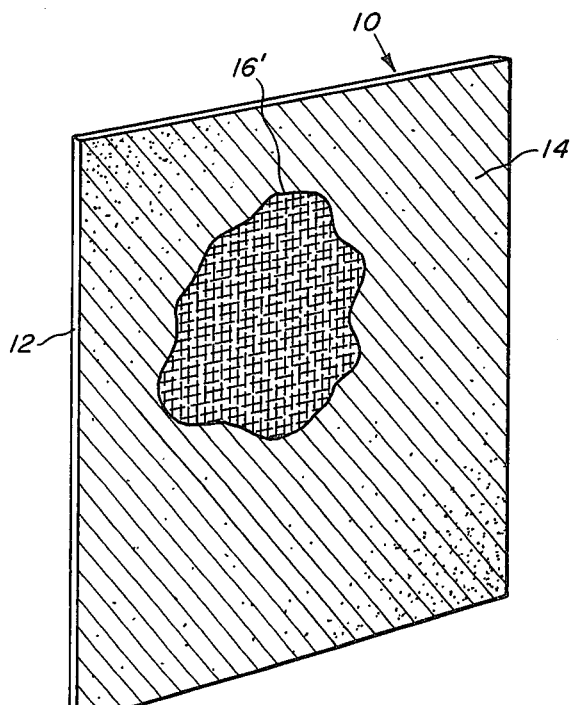
FIG. 3 is a view of the environmental quality indicator of FIG. 2 hours or days after exposure to a hazardous chemical.

In FIGS. 1-3 the numeral 10 generally designates an environmental quality indicator which is made up of a generally inert porous substrate. Suitable porous materials include sintered particles of polyethylene, polypropylene, nylon, and polyvinyl compounds. The pore sizes selected are determined by the ultimate drop size sensitivity desired. In testing for pesticides, a 30-micrometer pore-size polyethylene or polypropylene substrate, 12, has been found to be satisfactory. An indicator formulation is sprayed onto one side of porous substrate 12 and the resulting coating of indicator, 14, has been shaded to indicate a green surface. In FIG. 2, the numeral 16 designates a spot, shaded to indicate red, which initially results from the contacting of indicator 14 by a chemical. In FIG. 3, the numeral 16' designates the enlarged spot, shaded to indicate yellow, which is the result of spontaneous bleaching and the wicking effect of the chemical trapped within porous substrate 12. Highly volatile liquids will show proportionately less bleaching and spot enlarging effects than will non-volatile chemicals such as organophosphorous pesticides.

Figure 4:
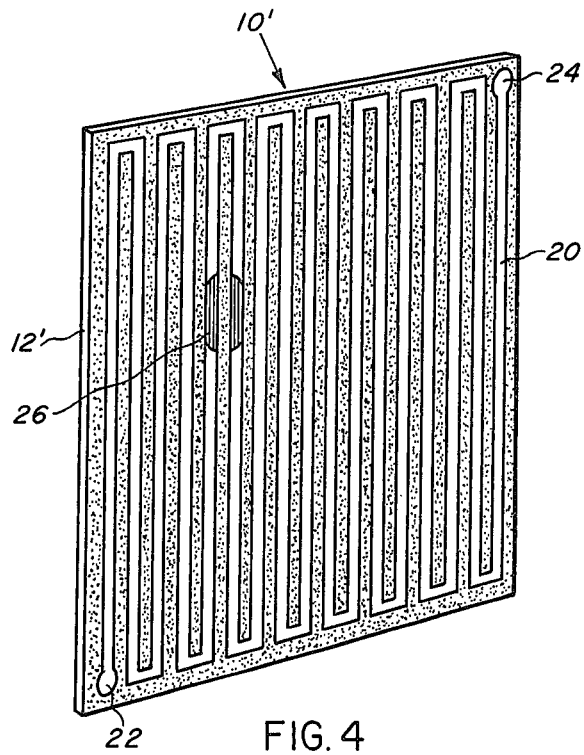
FIG. 4 is an isometric view of a second embodiment of the environmental quality indicator.

In FIG. 4, the numeral 10' generally designates a modified environmental quality indicator of the automatic or active type. Inert porous substrate 12' has a circuit 20 located thereon. In the form illustrated, silver particles are mixed with green indicator paint which produces a generally silver colored circuit 20 which connects contacts 22 and 24. Spot 26, shaded to indicate red, is produced when circuit 20 is contacted by the tested for chemical.

Figure 5:
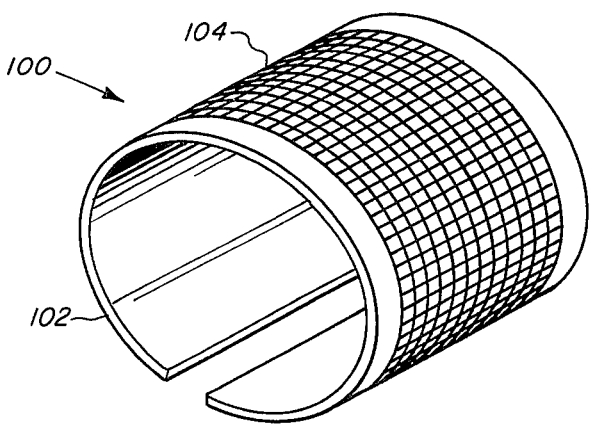
FIG. 5 is an isometric view of a third embodiment of the environmental quality indicator.
Figure 6:
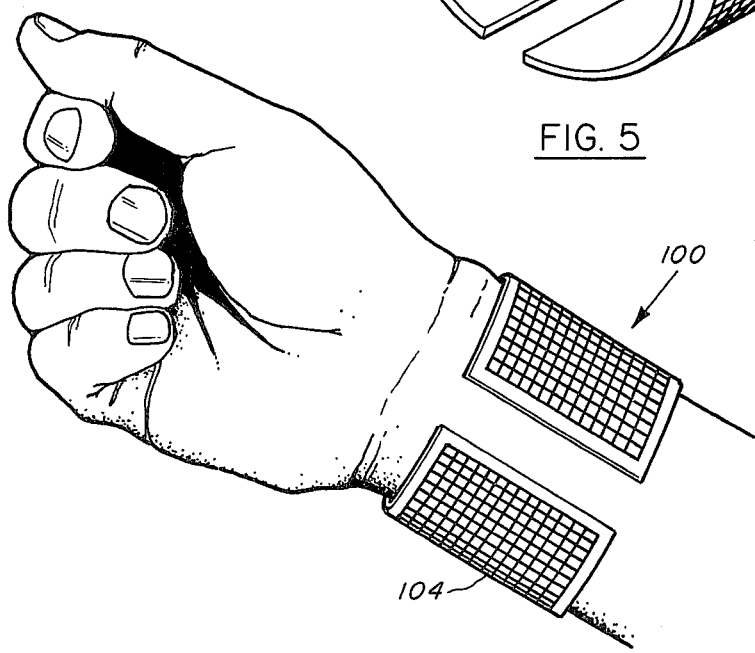
FIGS. 6 and 7 are views of the environmental quality indicator of FIG. 5 in use.
Figure 7:
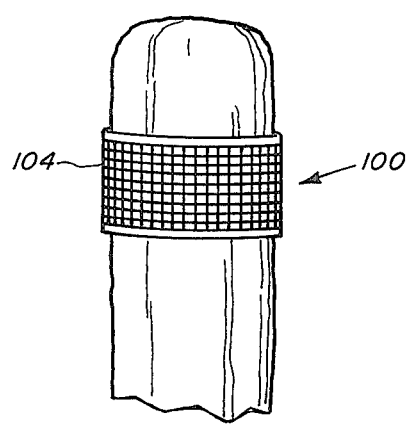

In FIGS. 5-7, the numeral 100 generally indicates an environmental quality indicator made up of a plastic base 102 which is deformed, with a memory, into a generally split-ring configuration for resilient attachment to a body member, as shown in FIG. 6, or to a post, fence or branch, as shown in FIG. 7. A topographically varying pattern 104 is formed on the outer surface of the base 102 for receiving an indicator formulation in a scuff and abrasion resistant environment.

Figure 8:
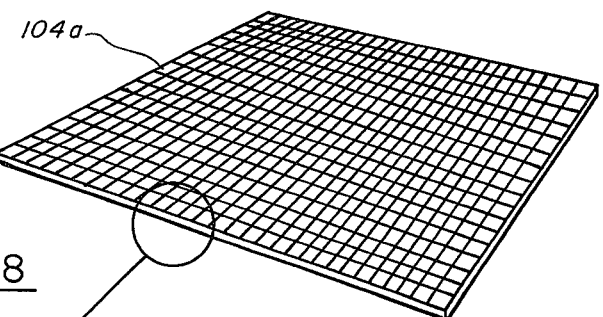
FIG. 8 is an isometric view of a first topographically varying pattern.
Figure 9:
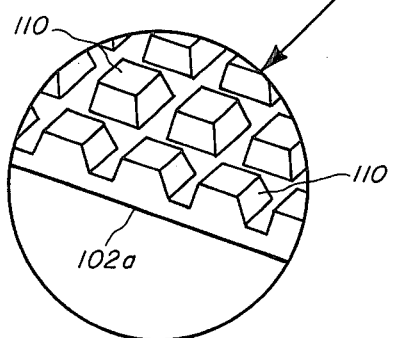
FIG. 9 is a partial view of the topographically varying pattern of FIG. 8 with an indicator formulation thereon.
Figure 9:
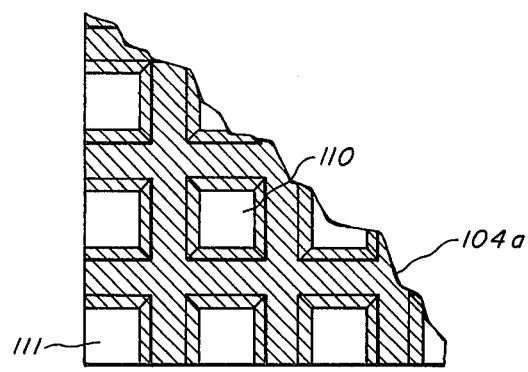

FIGS. 8 and 9 show one topographically varying pattern 104a which is suitable for use on the indicator 100 of FIGS. 5-7. The topographically varying pattern 104a is made up of a pattern of substantially uniformly located raised portions in the form of truncated prisms 110 extending up from base 102a. In FIG. 9, the scuff and abrasion resistant portion of the topographically varying pattern 104a formed by truncated prisms 110 has been shaded to indicate green to show an indicator formulation applied in the area protected from scuff and abrasion. The outermost surfaces 111 are shown as free of indicator formulation and can be achieved by wiping away the indicator formulation after application since surfaces 111 represent the scuff or abrasion level. If desired, surfaces 111 may be left covered with indicator formulation although it will be subject to scuff and abrasion which may falsely develop the indicator formulation. In such a case the protected surfaces would also be required to be developed to indicate contact with the tested-for substances.

Figure 10:
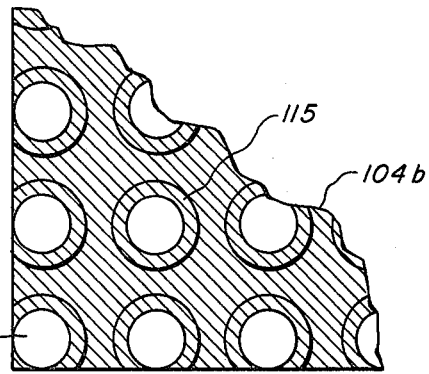
FIG. 10 is a partial view of a second topographically varying pattern with an indicator formulation thereon.

FIG. 10 shows a modified topographically varying pattern 104b shaded to show a green indicator formulation applied thereto. The topographically varying pattern 104b of FIG. 10 differs from topographically varying pattern 104a of FIG. 9 in the use of substantially uniformly located raised portions in the form of truncated cones 115 rather than truncated prisms 111.

Figure 11:
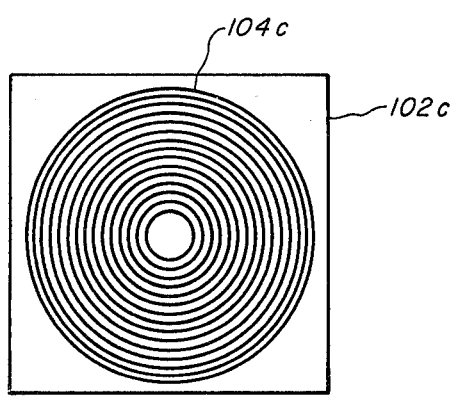
FIGS. 11 and 12 are views of third and fourth topographically varying patterns.

FIG. 11 illustrates another topographically varying pattern 104c which takes the form of a plurality of concentric grooves in the base 102c. Alternatively, a single spiralling groove such as is employed on phonograph records may be used.

Figure 12:
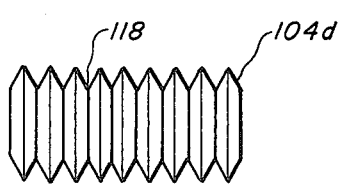

FIG. 12 illustrates an embodiment of the topographically varying pattern 104d in which the grooves 118 which define the protected surfaces may be either a series of circumferentially located grooves or a groove in the nature of a helix.

OPERATION

The environmental quality indicator 10 of FIGS. 1-3 is placed so that the coating of dye or indicator 14 is exposed to the environment. The indicator 10 may be placed in fields, hung from trees, floated in bodies of water, used as container covers, worn as badges or otherwise exposed to the environment. Suitable adhesives may be used to secure the indicators in place as in the case of a badge. When a chemical for which the test is being made contacts the coating 14 the green color changes to red, producing spot 16, about 10 seconds after first contact and then spontaneously bleaches to orange then yellow spot 16' as the spot enlarges continuously over a time period extending over a range of hours to days. The area of the color change indicates the amount of the chemical contacted. Since the indicator 10 is an inert porous substrate it presents a nonuniform surface with voids or pores which define recesses and surrounding particles which define substantially uniformed located elevated portions. These voids and surrounding particles together define a topographically varying surface on which the dye or indicator 14 can enter into the recesses or voids and be protected from physical environmental hazards by the surrounding particles, which define substantially uniformly located raised portions, while remaining freely exposed to chemical environmental hazards.

In the device of FIG. 4, an electrical power source is connected to contacts 22 and 24 which are electrically connected through the silver particles in the silver-loaded paint forming circuit 20. When the silver-loaded paint is contacted by the chemical tested for, the paint expands, separating the silver particles and changing the resistance between contacts 22 and 24. This change in resistance in the circuit 20 is used to activate an alarm or otherwise indicate contact with a chemical. Since the color indicating paint is used as the carrier for the silver particles, a red spot 26 is produced on the circuit 20 when contacted by the chemical to thereby give a visual indication in addition to the resistance change.

The environmental quality indicator 100 of FIGS. 5-7 is placed so that the coating of dye or indicator contained thereon is freely exposed to the environment. The indicator 100 is preferably held in place due to the resilience of base 102 as is shown in FIGS. 6 and 7. The specific configuration of the topographically varying surface 104 may take many forms as exemplified by 104a, 104b and 104c of FIGS. 8 and 9, 10 and 11, respectively. In each case the topographically varying surface is made up of two distinct components; an outer region, such as 111 of FIG. 9, which is made up of substantially uniformly located raised portions which are subject to scuff and abrasion and other physical environmental hazards; a lower or protected region, such as the portions of FIGS. 9 and 10 which are shaded to indicate green, which is protected from physical environmental hazards by the outer region, but which remains freely exposed to chemical environmental hazards.

The topographically varying surface 104d of FIG. 12 could be employed as the topographically varying surface 104 of FIGS. 5-7. Surface 104d would, however, be of particular use in the case of contact by flowing fluids. By presenting a streamlined profile rather than a generally rough and flat surface, as in the other embodiments, a more efficient contact of the fluid borne chemicals with the indicator or dye coating grooves 118 would result.

ENVIRONMENTAL QUALITY INDICATOR PREPARATION

The paint formulation used will depend upon the hazardous chemicals for which tests are being made. A satisfactory color indicating paint formulation for testing for organophosphorous chemicals such as malathion and parathion is as follows:

| Component | Type of Material | Proportion by Weight (%) |
| --- | --- | --- |
| Aroplaz 1700 (M60) (binder) | silicone modified alkyd resin | 8.4 |
| Arochem 90 (50% in VM & P) | ester gum modified phenolic resin | 10 |
| #920 Cadmium (yellow toner) | cadmium sulfide | 63 |
| VM & P (naphtha solvent) | aliphatic hydrocarbon | 5.2 |
| Heptane | aliphatic hydrocarbon | 10.2 |
| Red Dye | 1-(p'-nitro) phenylazo-2-amino naphthalene | 3.1 |
| 6% Cobalt Naphthenate | cobalt drier | .05 |
| 6% Manganese Naphthenate | manganese drier | .05 |

Aroplaz 1700 (M60) and Arochem 90 are products of Ashland Chemical Company. Variations in the ingredients of this formulation are possible while still achieving a usable environmental quality indicator. For example, it would be possible to make an indicator paint with only a binder, dye, toner and solvents.

For the conductive type of indicator paint two approaches are possible. First, conductive materials such as flakes or particles of silver, copper, iron, aluminum, carbon or graphite may be added directly to the green indicator paint described above. The amount of conductive material to be added depends upon the range of conductivity desired and the electronics to be used to indicate the presence of hazardous chemicals. In a device of the type illustrated in FIG. 4, 80% conductive silver flakes has been found to be satisfactory. Second, conductive particles can be mixed directly in the binder Aroplaz 1700 (M60). This results in a highly conductive paint which is extremely sensitive to pesticides.

Several techniques have been used in applying indicator dyes and paints to make environmental quality indicators and these include spraying, dipping and silk-screening. Other techniques such as printing either by letter press or rotogravure may also be used.

To prepare an environmental quality indicator of the type illustrated in FIGS. 1-3, a porous substrate such as either low or high density polyethylene is coated with an indicator paint. The coating may be sprayed on the substrate from a paint sprayer, the substrate may be dipped into the indicator paint, or the substrate may be otherwise coated. Spraying appears to be the most economical method for applying the indicator paint in a device of the FIG. 1 type. The coated surfaces of the recesses or voids forming the protected portion of the topographically varying surface of the substrate will be below the scuff and abrasion level and will, therefore, be protected from physical environmental hazards while remaining freely exposed to chemical environmental hazards.

To prepare an environmental quality indicator of the type illustrated in FIG. 4 a silk-screening or similar technique is used to produce an undulating circuit, such as 20, on the porous substrate. Spraying or dipping may also be used if the coated substrate is then cut to form a circuit element such as a 1/16 inch by 2 inch strip.

To prepare an environmental quality indicator of the types illustrated in FIGS. 5-12, either a castable or moldable material is cast or molded in the desired configuration with the desired topographically varying pattern, or a heat or pressure deformable material is heat or pressure deformed into the desired configuration with the desired topographically varying pattern. The material of the substrate may be metal or polymeric resin such as nylon and cellulose acetate or any other materials having the desired properties under the conditions of use. Adherence of the indicator formulation can be enhanced by providing a suitable finish on the substrate such as a matte finish for a Mylar substrate. The topographically varying patterns may be formed by causing depressions in the surface of the substrate or by causing the surface material to be extruded through the orifices of a die under heat and/or pressure. Where the topographically varying surface of the substrate is produced by causing depressions on one surface of the substrate and elevations on the opposite surface two benefits can result: (1) the corresponding depressions and elevations provide a method of securing the indicator in place due to their nestable nature and this can be employed to secure a device of the type illustrated in FIGS. 5-7; and (2) if the formation of the depression and corresponding elevation also causes a puncturing of the substrate, the resulting porosity of the otherwise nonporous substrate permits "breathing" of the underlying skin, etc.

The environmental indicators described above are subject to certain interferences which will produce a spurious color and/or a resistance change. Extreme heat as from a burning cigarette or match will produce the initial color change illustrated in FIGS. 2 and 4 but the development of the spot, as in the case of spot 16 of FIG. 2 progressing to spot 16' of FIG. 3, will not occur. Volatile liquids such as gasoline with certain additives and acetone may also produce a color change. Where a porous substrate is used, the substrate's capillary and chromotographic properties minimize such interference since the chemicals of this type are quickly driven into the detector, in most cases without producing a change in color or resistance. Further, the rapid evaporation of the liquid prevents the normal pattern enlargement of detector "spots" which does occur with the less-volatile target chemicals.

It will be obvious to those skilled in the art that the advantages of the present invention are applicable to other uses such as thermal resistivity circuits which can be used in the same manner as the described electrical circuit.

Although preferred embodiments of the present invention have been illustrated and described, other changes will occur to those skilled in the art. While the substrate has been disclosed as below the indicator, the term as used herein is intended to include carriers or supports for the indicator whether below or above the same. Also, the topographically varying surface may be in the form of projections or depressions and may be, for example, of hemispherical, cylindrical, and cubic shapes and the grooves may be, for example, in the form of concentric circles, circumferential grooves, spiral and helix patterns. It is therefore intended that the scope of the present invention is to be limited only by the scope of the appended claims.

We claim:

1. A waterproof, scuff-resistant environmental quality indicator for indicating the presence of pesticides in the environment and which normally is abrasion and scuff developable to give the same initial color and/or resistance change as the said pesticides being monitored or tested, comprising:

an environmentally inert, weather-resistant substrate having a topographically varying surface including substantially uniformly located raised portions defining a scuff and abrasion level, the remainder of said topographically varying surface defining a relieved portion beneath said scuff and abrasion level; and an abrasion and scuff-developable indicator formulation which gives the same initial color and/or resistance changes as the said pesticides, said formulation for detecting pesticides applied to at least said relieved portion of said substrate whereby said indicator formulation applied to said relieved portion of said substrate is protected by said raised portions from being abrasion-developed while remaining freely exposed to the environment for the indicating of the presence of pesticides.

2. The indicator of claim 1 wherein the indicator formulation includes a color indicating paint which changes color when contacted by a pesticide.

3. The indicator of claim 2 wherein the indicator formulation further includes conductive particles whose conductivity therebetween changes when contacted by a pesticide.

4. The indicator of claim 3 wherein the indicator formulation is applied to the substrate in a circuitous pattern which extends over a substantial portion of the substrate between two contacts for attachment to indicating devices.

5. The indicator of claim 1 wherein the substrate is polyethylene.

6. The indicator of claim 1 wherein the substrate is polypropylene.

7. The indicator of claim 1 wherein the substrate is sintered.

8. The indicator of claim 1 wherein the indicator formulation includes conductive particles.

9. The indicator of claim 8 wherein the indicator formulation is applied to the substrate in a circuitous pattern which extends over a substantial portion of the substrate between two contacts for attachment to indicating devices.

10. The indicator of claim 1 wherein said substrate is porous to permit the wicking of contacting pesticides into said substrate.

11. The indicator of claim 1 wherein said substrate is resiliently deformable to permit said indicator to be located and held in position.

12. A waterproof, scuff-resistant environmental quality indicator for indicating the presence of pesticides in the environment and which normally is abrasion and scuff developable to give the same initial color and/or resistance change as the said pesticides being monitored or tested, comprising:

an environmentally inert, weather-resistant porous substrate having substantially uniformly located portions projecting therefrom and defining the pores on the surface of said porous substrate; and an abrasion and scuff-developable indicator formulation for detecting pesticides applied to a portion of said substrate such that said pores of said portion of said substrate receive developable quantities of said indicator formulation which gives the same initial color and/or resistance changes as the said pesticides, said formulation within said pores of said portion of said substrate whereby said projecting portions surrounding said pores containing said indicator formulation protect said indicator formulation in said pores from being abrasion-developed while remaining freely exposed to the environment.

13. A waterproof, scuff-resistant indicator which normally is abrasion and scuff developable to give the same initial color and/or resistance changes as hazardous chemicals being monitored or tested, comprising:

an environmentally inert, weather-resistant substrate having a topographically varying surface including substantially uniformly located raised portions defining a scuff and abrasion level, the remainder of said topographically varying surface defining relieved portions beneath said scuff and abrasion level; and an abrasion developable indicator formulation which gives the same initial color and/or resistance changes as the hazardous chemicals being monitored or tested, said formulation applied to at least said relieved portions of said substrate such that said relieved portions of said substrate receive developable quantities of said indicator formulation whereby said indicator formulation applied to said relieved portions is protected against being developed by abrasion while remaining freely exposed to the environment.

14. The indicator of claim 13 wherein said substrate is porous.

15. The indicator of claim 13 wherein the indicator formulation includes conductive particles.

16. The indicator of claim 13 wherein said substrate is resiliently deformable to permit said indicator to be located and held in place.

17. A waterproof, scuff-resistant indicator which normally is abrasion and scuff developable to give the same initial color and/or resistance changes as hazardous chemicals being monitored or tested, comprising:

an environmentally inert, weather-resistant porous substrate having substantially uniformly located portions projecting therefrom and defining the pores of said porous substrate; and an abrasion developable indicator formulation which gives the same initial color and/or resistance changes as the hazardous chemicals being monitored or tested, said formulation applied to a portion of said substrate such that said pores of said portion of said substrate receive developable quantities of said indicator formulation within said pores of said portion of said substrate whereby said projecting portions surrounding said pores containing said indicator formulation protect said indicator formulation in said pores from being developed by abrasion while remaining freely exposed to the environment.

18. A waterproof, scuff-resistant indicator which normally is abrasion and scuff developable to give the same initial color and/or resistance changes as hazardous chemicals being monitored or tested, comprising:

an inert porous substrate of particles having an outer surface defined by exteriorly located particles which present a topographically varying surface having relieved portions defined by pores and interstices formed between said exteriorly located particles; and an indicator formulation which gives the same initial color and/or resistance changes as the hazardous chemicals being monitored or tested, said formulation applied to a portion of the topographically varying surface of said substrate including said relieved portions which are beneath scuffing and abrasion level to thereby protect said indicator formulation from scuffing and abrasion while remaining freely exposed to the environment.

19. The indicator of claim 18 wherein the particles of said substrate are sintered.

20. A waterproof, scuff-resistant environmental quality indicator for indicating the presence of pesticides in the environment and which normally is abrasion and scuff developable to give the same initial color and/or resistance change as the said pesticides being monitored or tested, comprising only:

an environmentally inert, weather-resistant substrate having a topographically varying surface including substantially uniformly located raised portions defining a scuff and abrasion level, the remainder of said topographically varying surface defining a relieved portion beneath said scuff and abrasion level; and an abrasion and scuff-developable indicator formulation for detecting pesticides applied to at least said relieved portion of said substrate whereby said indicator formulation applied to said relieved portion of said substrate is protected by said raised portions from being abrasion-developed while remaining freely exposed to the environment for the indicating of the presence of pesticides.

* * * * *

UNITED STATES PATENT AND TRADEMARK OFFICE
CERTIFICATE OF CORRECTION

PATENT NO. : 4,092,119

DATED : May 30, 1978

INVENTOR(S) : Robert E. Baier and Vito A. DePalma

It is certified that error appears in the above-identified patent and that said Letters Patent are hereby corrected as shown below:

In claim 12 at line 12 insert --which gives the same initial color and/or resistance changes as the said pesticides, said formulation-- after "tion" and before "for"; In claim 12 at lines 15-17 delete "which gives the same initial color and/or resistance changes as the said pesticides, said formulation". In claim 20 at line 15 insert --which gives the same initial color and/or resistance changes as the said pesticides, said formulation-- after "tion" and before "for".

Signed and Sealed this

Fourteenth Day of November 1978

[SEAL]

Attest:

RUTH C. MASON
Attesting Officer

DONALD W. BANNER
Commissioner of Patents and Trademarks